United States Patent [19]

DesLauriers et al.

[11] Patent Number: 5,319,091
[45] Date of Patent: Jun. 7, 1994

[54] PROCESS FOR SULFUR CONTAINING DERIVATIVES OF HYDROXYPHENYL/BENZOTRIAZOLES

[75] Inventors: Paul J. DesLauriers; Paritsoh K. Das; Darryl R. Fahey, all of Bartlesville, Okla.; Frederick J. Cornforth, Sweeny, Tex.

[73] Assignee: Phillips Petroleum Company, Bartlesville, Okla.

[21] Appl. No.: 981,024

[22] Filed: Nov. 24, 1992

[51] Int. Cl.$^5$ .............................................. C07D 249/20
[52] U.S. Cl. ..................................... 548/259; 548/260
[58] Field of Search ..................... 548/259; 568/27

[56] References Cited

U.S. PATENT DOCUMENTS

| | | |
|---|---|---|
| 3,004,896 | 10/1961 | Heller et al. . |
| 3,849,499 | 11/1974 | Malievsky et al. ............... 568/27 |
| 4,609,712 | 9/1986 | Evans et al. ...................... 568/27 |
| 4,853,471 | 8/1989 | Rody et al. ....................... 548/261 |
| 4,871,793 | 10/1989 | Nakahara et al. ............... 524/91 |

FOREIGN PATENT DOCUMENTS

| | | |
|---|---|---|
| 62-288630 | 12/1987 | Japan . |
| 944843 | 12/1963 | United Kingdom ............ 548/259 |

*Primary Examiner*—Donald G. Daus
*Attorney, Agent, or Firm*—Lucas K. Shay

[57] ABSTRACT

A composition that, when present in a polymer matrix, reduces the deleterious effect of UV light absorption by the polymer is provided, which comprises a sulfur-containing derivative of hydroxyphenylbenzotriazole having the formula of:

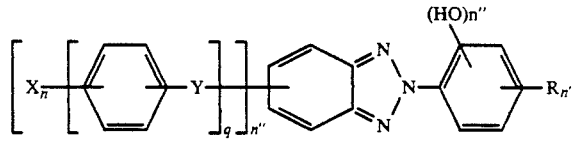

wherein each X is selected from the group consisting of hydrogen, halogens, cyano, alkyl, phenyl group, biphenyl group, arylthio, amine, ketone, aldehyde, alkoxy, hydroxy, carboxylic acid group, oligomer and combinations thereof and can have carbon atoms up to about 20; n is a whole number from 1 to 5; n' is a whole number from 0 to 4; n" is a whole number from 1 to 2 and each n" can be the same or different; q is an integer from 1 to 10; each Y is selected from the group consisting of —S(O) (O)—, —S(O)—, and —S—; each R can be selected from the group consisting of hydrogen, alkyl group, alkenyl group, aralkyl group, alkaryl group, and combinations thereof and can have 0 to about 10 carbon atoms; each OH group can be at either the 2'- or the 6'-position, or both. Also provided are a composition comprising the sulfur-containing derivative, a process for preparing the derivative, a composition comprising a polymer chemically bonded to the derivative, and a process for preparing the composition which comprises a polymer chemically bonded to the derivative.

50 Claims, No Drawings

PROCESS FOR SULFUR CONTAINING DERIVATIVES OF HYDROXYPHENYL/BENZOTRIAZOLES

FIELD OF THE INVENTION

The present invention relates to a composition comprising a sulfur-containing derivative of hydroxyphenylbenzotriazole, a process for synthesizing the derivative, a composition comprising a polymer chemically bonded to the derivative, and a process for synthesizing the polymer chemically bonded to the derivative.

BACKGROUND OF THE INVENTION

Engineering plastics such as poly(arylene sulfide) resins are excellent polymers having good thermal stability, chemical resistance, flame resistance, and electrical insulation properties. These physical properties make them useful as, for example, coatings for pipes, tanks, or pumps, in manufacturing extruded articles, films, sheets, or fibers, and in injection molded products for electronic or electrical applications.

Generally, these polymers, when newly made, have a pleasant and attractive appearance due to extremely low coloration. They are, however, known to have a very high absorption of light in the ultraviolet (hereinafter referred to as UV) region. Upon being exposed to solar or UV rays, these polymers darken in color. Furthermore, absorption of UV light may result in a decrease in some mechanical properties of the polymers.

The common method of stabilizing a polymer against light is by mixing it with a protective agent. In comparison to coating finished products (films and fibers) with stabilizers or incorporation of photostabilizing functionalities into the polymer, the method based on bulk addition of a protective agent is usually straightforward and can be technologically simple. To achieve optimal action without seriously affecting desired properties of a given polymer, a great deal of care, however, is called for in selecting the type and amount of a compatible additive useful as a protective agent.

Certain metals, metal compounds (including oxides, carbonates and sulfides), transition metal complexes, organotin azolides, pyrene derivatives, non-sulfur-containing hydroxyphenylbenzotriazole derivatives and special aniline-nitrobenzene dyes (nigrosins) have been claimed to improve UV stability of polymers and/or reduce radical formation in polymers. For example, non-sulfur-containing hydroxyphenylbenzotriazole derivatives when added to a poly(arylene sulfide) polymer work well as stabilizers to reduce the deleterious effects of ultraviolet exposure upon the polymer. Unfortunately, the high melt processing temperatures of the polymer lead to loss of these stabilizers through evaporation. The degree of UV light stabilization afforded to the polymer by these known non-sulfur-containing hydroxyphenylbenzotriazole derivatives is thereby appreciably limited.

Therefore, it would be a significant contribution to the art if a new hydroxyphenylbenzotriazole derivative that is less volatile at the temperatures used to process tile polymers and affords a higher degree of protection against UV light can be developed.

SUMMARY OF THE INVENTION

An object of the present invention is to provide a new hydroxyphenylbenzotriazole derivative that reduces the deleterious effect of UV light on a polymer. Another object of the invention is to provide a process for synthesizing the hydroxyphenylbenzotriazole derivative. A further object of the invention is to provide a process for synthesizing the hydroxyphenylbenzotriazole derivative in high yield. Yet another object of the invention is to provide a hydroxyphenylbenzotriazole derivative that is stable at the high melt processing temperatures of the polymers. Yet still another object of the invention is to provide a hydroxyphenylbenzotriazole derivative that has low volatility at the high melt processing temperatures of the polymers. Still a further object of the invention is to provide a process for stabilizing polymers against UV light absorption. Yet still a further object is to provide a polymer composition that is UV stable and a process for producing the composition. Other objects, advantages and features will become more apparent as the invention is more fully disclosed hereinbelow.

According to a first embodiment of the present invention, a composition that, when present in a polymer matrix, reduces the deleterious effect of UV light absorption by the polymer is provided, which comprises a sulfur-containing derivative of hydroxyphenylbenzotriazole having the formula of:

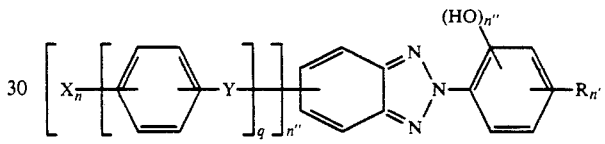

wherein each X is a substituent selected from the group consisting of hydrogen, chlorine, bromine, iodine, fluorine, cyano, alkyl, phenyl group, biphenyl group, arylthio, amine, ketone, aidehyde, alkoxy, hydroxy, carboxylic acid group, oligomer and combinations thereof; unless otherwise indicated, each X, if it is a carbon-containing substituent, can have carbon atoms from 1 to about 20; n is a whole number from 1 to 5; n' is a whole number from 0 to 4; n" is a whole number from 1 to 2 and each n" can be the same or different; q is an integer from 1 to 10; Y is selected from the group consisting of —S(O)(O)—, —S(O)—, and —S—; each R can be the same or different and each can be selected from the group consisting of hydrogen, alkyl group, alkenyl group, aralkyl group, alkaryl group, and combinations thereof; when R has more than 2 carbon atoms, it can be linear, branched, or cyclic; each R, unless otherwise indicated, can have 0 to about 10 carbon atoms; each OH group can be at either the 2'- or the 6'-position, or both; and X, Y, and R can be at any available position of the arylene rings.

According to a second embodiment of the invention a process for stabilizing a polymer against the deleterious effect of UV light absorption is provided which comprises contacting the polymer with a sulfur-containing derivative of hydroxyphenylbenzotriazole having the formula of:

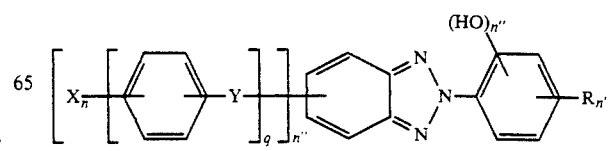

wherein each X is a substituent selected from the group consisting of hydrogen, chlorine, bromine, iodine, fluorine, cyano, $C_1$-$C_{20}$ alkyl, phenyl group, biphenyl group, arylthio, amine, ketone, aldehyde, $C_1$-$C_{20}$ alkoxy, hydroxy, carboxylic acid group, oligomer and mixtures thereof; unless otherwise indicated, each X, if it is a carbon-containing constituent, can have carbon atoms from 1 to about 20; n is a whole number from 1 to 5; n' is a whole number from 0 to 4; n" is a whole number from 1 to 2 and each n" can be the same or different; q is an integer from 1 to 10; each Y is selected from the group consisting of —S(O)(O)—, —S(O)—, —S—, and combinations thereof; each R can be the same or different and each can be selected from the group consisting of hydrogen, alkyl group, alkenyl group, aralkyl group alkaryl group, and combinations thereof; when R has more than 2 carbon atoms, it can be linear, branched, or cyclic; each R, unless otherwise indicated, can have 0 to about 10 carbon atoms; each OH group can be at either the 2'- or the 6'-position, or both; and X, Y, and R can be at any available position of the arylene rings.

According to a third embodiment of the present invention, a process for synthesizing a sulfur-containing derivative of hydroxyphenylbenzotriazole having the formula of:

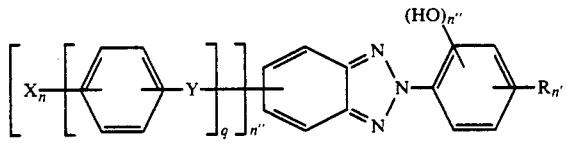

is provided which comprises: (1) contacting a sulfur-containing aromatic compound selected from the group consisting of thiophenolate anion and thiophenolic compound with a halo-substituted hydroxyphenylbenzotriazole derivative having the formula of:

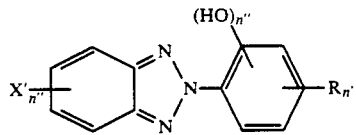

in the presence of a polar organic compound to form an aryl sulfide derivative of hydroxyphenylbenzotriazole; (2) contacting the aryl sulfide derivative of hydroxyphenylbenzotriazole with an oxidizing agent to form either an aryl sulfoxide or an aryl sulfone derivative of hydroxyphenylbenzotriazole, or mixture of aryl sulfoxide and aryl sulfone derivatives of hydroxyphenylbenzotriazole; and (3) recovering the aryl sulfoxide derivative of hydroxyphenylbenzotriazole, the aryl sulfone derivative of hydroxyphenylbenzotriazole, or the mixture of aryl sulfoxide and aryl sulfone derivatives of hydroxyphenylbenzotriazole; wherein each X is a substituent selected from the group consisting of hydrogen, chlorine, bromine, iodine, fluorine, cyano, alkyl, phenyl group, biphenyl group, arylthio, amine, ketone, aldehyde, alkoxy, hydroxy, carboxylic acid group, oligomer, and combinations thereof; unless otherwise indicated, each X, if it is a carbon-containing constituent, can have carbon atoms from 1 to about 20; n is a whole number of 1 to 5; n' is a whole number of 0 to 4; n" is a whole number from 1 to 2 and each n" can be the same or different; q is an integer from 1 to 10; each Y is selected from the group consisting of —S(O)(O)—, —S(O)—, —S—, and combinations thereof; each R can be the same or different and each can be selected from the group consisting of hydrogen, alkyl group, alkenyl group, an aralkyl group, an alkaryl group and combinations thereof; when R has 2 or more carbon atoms, it can be linear, branched, or cyclic; each R, unless otherwise indicated, can have 0 to about 10 carbon atoms; each X' is selected from the group consisting of chlorine, bromine, iodine, fluorine; each OH group can be at either the 2'- or the 6'-position, or both; and X, Y, R, and X' can be at any available position of the arylene rings.

According to s fourth embodiment of the present invention, a UV light-stable polymer composition is provided which comprises a polymer chemically bonded to a sulfur-containing derivative of hydroxyphenylbenzotriazole where the composition has the formula of:

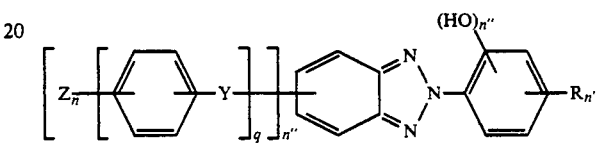

wherein each Z is a polymer; n is a whole number of 1 to 5; n' is a whole number of 0 to 4; n" is a whole number from 1 to 2 and each n" can be the same or different; q is an integer of 1 to 10; each Y is selected from the group consisting of —S(O)(O)—, —S(O)—, —S—, and mixtures thereof; each R can be the same or different and each can be selected from the group consisting of hydrogen, alkyl group, alkenyl group, an aralkyl group, an alkaryl group, and combinations thereof; when R has more than 2 carbon atoms, it can be linear, branched or cyclic; each R, unless otherwise indicated can have 1 to 10 carbon atoms; each OH group can be at either the 2'- or the 6'-position, or both; and Z, Y, and R can be at any available position of the arylene rings.

According to a fifth embodiment of the invention, a process is provided for synthesizing a UV light-stable polymer composition where the polymer is chemically bonded to a sulfur-containing derivative of hydroxyphenylbenzotriazole and the composition has the formula of:

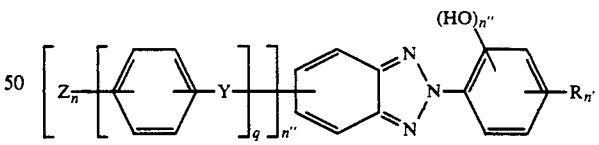

wherein each Z is a polymer; n is a whole number of 1 to 5; n' is a whole number of 0 to 4; n" is a whole number from 1 to 2 and each n" can be the same or different; q is an integer of 1 to 10; each Y is selected from the group consisting of —S(O)(O)—, —S—, and mixtures thereof; each R can be the same or different and are each selected from the group consisting of hydrogen, $C_1$-$C_{10}$ alkyl group, $C_2$-$C_{10}$ alkenyl group, an aralkyl group, an alkaryl group, and combinations thereof; when R has more than 2 carbon atoms, it can be linear, branched, or cyclic; each R, unless otherwise indicated, can have 0 to about 10 carbon atoms; each OH group can be at either the 2'- or the 6'-position, or both; and Z, Y, and R can be at any available position of the arylene rings; wherein the process comprises contacting a halo-substituted sulfur-containing derivative of hydroxyphenylbenzotriazole with at least one halogenated aromatic monomer and a sulfur source under polymerization conditions to synthesize the polymer.

DETAILED DESCRIPTION OF INVENTION

According the first embodiment of the invention, a composition that, when present in a polymer matrix, reduces the effect of UV light absorption on a polymer comprises a sulfur-containing derivative of hydroxyphenylbenzotriazole having the formula of:

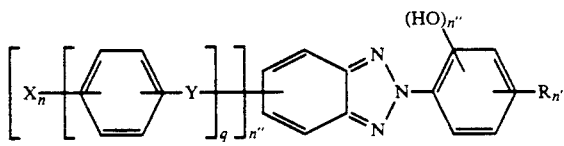

wherein each X is a substituent selected from the group consisting of hydrogen, chlorine, bromine, iodine, fluorine, cyano, alkyl, phenyl group, biphenyl group, arylthio amine, ketone, aldehyde, alkoxy, hydroxy, carboxylic acid group, oligomer and mixtures thereof; unless otherwise indicated, each X, if it is a carbon-containing substituent, can have 1 to about 20 carbon atoms; n is a whole number of 1 to 5; n' is a whole number of 0 to 4; n'' is a whole number from 1 to 2 and each n'' can be the same or different; q is an integer of 1 to 10; each Y is selected from the group consisting of —S(O)(O)—, —S(O)—, —S—, and combinations thereof; each R can be the same or different and each can be selected from the group consisting of hydrogen, alkyl group, alkenyl group, an aralkyl group, an alkaryl group, and combinations thereof; each R can have 0 to about 10 carbon atoms; when R has more than 2 carbon atoms, it can be linear, branched, or cyclic; each OH group can be at either the 2'- or the 6'-position, or both; and X, Y, and R can be at any available position of the arylene rings.

The term "oligomer" is used herein to refer to an organic molecule consisting of only a few monomer units, generally from 2 to about 10 repeating units. Examples of oligomers are dimer, trimer, tetramer, octamer, and mixtures thereof. The term "polymer matrix" refers to a composition comprising at least one polymer. The composition can be, for example, a dry blend or melt blend.

Suitable sulfur-containing derivatives of hydroxyphenylbenzotriazole of the present invention include, but are not limited to, 2-(3',5'-di-tert-butyl-2'-hydroxyphenyl)-5-(phenylthio)benzotriazole, 2-(3',5'-di-tert-butyl-2'-hydroxyphenyl)-5-(phenylsulfinyl)benzotriazole, 2-(3',5'-di-tert-butyl-2'-hydroxyphenyl)-5-(phenylsulfonyl)benzotriazole, 2-(2'-hydroxyphenyl)-5-(phenylthio)benzotriazole, 2-(2'-hydroxyphenyl)-5-(phenylsulfinyl)benzotriazole, 2-(2'-hydroxyphenyl)-5-(phenylsulfonyl)benzotriazole, 2-(3',5'-di-tert-butyl-2'-hydroxylphenyl)-5-(4''-aminophenylthio)benzotriazole, 2-(3',5'-di-tert-butyl-2'-hydroxylphenyl)-5-(4''-aminophenylsulfinyl)benzotriazole, 2-(3',5'-di-tert-butyl-2'-hydroxylphenyl)-5-(4''-aminophenylsulfonyl)benzotriazole, 2-(3',5'-di-tert-cumyl-2'-hydroxyphenyl)-5-(phenylthio)benzotriazole, 2-(3',5'-di-tert-cumyl-2'-hydroxyphenyl)-5-(phenylsulfinyl)benzotriazole, 2-(3',5'-di-tert-cumyl-2'-hydroxyphenyl)-5-(phenylsulfonyl)benzotriazole, 2-(3',5'-di-tert-butyl-2'-hydroxylphenyl)-5-(4''-bromophenylthio)benzotriazole, 2-(3',5'-di-tert-butyl-2'-hydroxylphenyl)-5-(4''-bromophenylsulfinyl)benzotriazole, 2-(3',5'-di-tert-butyl-2'-hydroxylphenyl)-5-(4''-bromophenylsulfonyl)benzotriazole, and mixtures thereof.

The preparation of the sulfur-containing derivatives of hydroxyphenylbenzotriazole of the present invention is described hereinbelow in the third embodiment of the invention.

In the second embodiment of the present invention, a process for stabilizing a polymer against the deleterious effect of light, especially UV light absorption, is provided which comprises contacting the polymer with a sulfur-containing derivative of hydroxyphenylbenzotriazole. The scope of the sulfur-containing derivative of hydroxyphenylbenzotriazole is the same as that described in the first embodiment of the invention.

The term "polymer" used herein refers to homopolymers, copolymers, terpolymers and tetrapolymers. It further refers to a high molecular weight organic compound whose structure can be represented by generally more than about 10 repeating monomer units of simple molecules. The polymers can be synthesized by methods well-known in the art. Generally, the monomer units of the oligomer as described hereinabove in the first embodiment of the invention are the same as those comprising the polymer to be stabilized.

The polymer suitable for the present invention can be any polymer that is sensitive to UV light. Any physical forms of the polymer can be stabilized by the sulfur-containing derivatives of hydroxyphenylbenzotriazole of the present invention. The physical forms include, but are not limited to pellets, powders, fibers, films, sheets, molded articles, and mixtures thereof. Examples of suitable polymers include, but are not limited to, poly(phenylene sulfide)s, poly(phenylene sulfone)s, poly(phenylene ether)s, poly(phenylene ketone)s, poly(phenylene ether ketone)s, poly(phenylene disulfide)s, poly(phenylene sulfide sulfone)s, poly(phenylene sulfide ketone)s, poly(phenylene sulfide disulfide)s, and copolymers thereof; polyethylene, polypropylene, poly(4-methyl-1-pentene), and copolymers thereof; polycarbonate; polyethylene terephthalate; and mixtures thereof.

The presently preferred polymer is a poly(phenylene sulfide) which is commercially available from Phillips Petroleum Company, Bartlesville, Okla.

The process of the second embodiment of the invention can be carried out by a variety of means. The simplest means is to mix the polymer with the sulfur-containing derivative of hydroxyphenylbenzotriazole. Mixing can be done by dry blending before melt processing, melt blending or solvent-assisted methods. These mixing methods are well-known in the art.

The amount of a sulfur-containing derivative of hydroxyphenylbenzotriazole required generally depends on the type of polymer and the desired degree of protection against ultraviolet light. A suitable amount is in the range of from about 0.01 to about 50 weight %, preferably from about 0.1 to about 20 weight %, and most preferably from 0.5 to 15 weight % based on total weight of the final composition.

In the first step of the third embodiment of the invention, the synthesis of the sulfur-containing derivative of hydroxyphenylbenzotriazole of the first embodiment of the invention, a halo-substituted hydroxyphenylbenzotriazole derivative having the formula of:

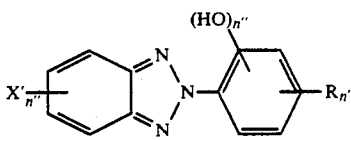

is contacted with a sulfur-containing aromatic compound in the presence of a polar organic compound at an elevated temperature; wherein each X' is a chlorine, bromine, iodine, fluorine or a suitable leaving group capable of being substituted by the sulfur-containing aromatic compound; n' is an integer from 0 to 4; n" is an integer from 1 to 2 and each n" can be the same or different; each R can be the same or different and each can be selected from the group consisting of hydrogen, alkyl group, alkenyl group, an aralkyl group, an alkaryl group and mixtures thereof; each R can have 0 to about 10 carbon atoms; and when R has more than 2 carbon atoms, it can be linear, branched or cyclic; each OH group can be at the 2'- or the 6'-position, or both. Additionally, X' and R can be at any available position of the arylene rings. Examples of suitable halo-substituted hydroxyphenylbenzotriazole derivatives include, but are not limited to, 2-(3',5'-di-tert-butyl-2'-hydroxyphenyl)-5-chlorobenzotriazole, 2-(3',5'-di-tert-butyl-2'-hydroxyphenyl)-5-bromobenzotriazole, 2-(3',5'-di-tert-butyl-2'-hydroxyphenyl)-5-fluorobenzotriazole, 2-(3',5'-di-tert-butyl-2'-hydroxyphenyl)-5,6-dichlorobenzotriazole, 2-(3',5'-di-tert-butyl-2'-hydroxyphenyl)-5,6-dibromobenzotriazole, 2-(3',5'-di-tert-butyl-2'-hydroxyphenyl)-5,6-difluorobenzotriazole, 2-(3',5'-di-n-butyl-2'-hydroxyphenyl)-5-chlorobenzotriazole, 2-(3',5'-di-n-butyl-2'-hydroxyphenyl)-5-bromobenzotriazole, 2-(3',5'-di-n-butyl-2'-hydroxyphenyl)-5-fluorobenzotriazole, 2-(3',5'-di-i-propyl-2'-hydroxyphenyl)-5-chlorobenzotriazole, 2-(3',5'-di-i-propyl-2'-hydroxyphenyl)-5-bromobenzotriazole, 2-(3',5'-di-i-propyl-2'-hydroxyphenyl)-5-fluorobenzotriazole, 2-(3',5'-di-i-propyl-2'-hydroxyphenyl)-5,6-dichlorobenzotriazole, 2-(3',5'-di-i-propyl-2'-hydroxyphenyl)-5,6-dibromobenzotriazole, 2-(3',5'-di-i-propyl-2'-hydroxyphenyl)-5,6-difluorobenzotriazole, 2-(3',5'-dimethyl-2'-hydroxypheny)-5-chlorobenzotriazole, 2-(3',5'-dimethyl-2'-hydroxyphenyl)-5-bromobenzotriazole, 2-(3',5'-dimethyl-2'-hydroxyphenyl)-5-fluorobenzotriazole, 2-(3',5'-dimethyl-2'-hydroxyphenyl)-5,6-dichlorobenzotriazole, 2-(3',5'-dimethyl-2'-hydroxyphenyl)-5,6-dibromobenzotriazole, 2-(3',5'-dimethyl-2'-hydroxyphenyl)-5,6-difluorobenzotriazole, 2-(3',5'-dibenzyl-2'-hydroxyphenyl)-5-chlorobenzotriazole, 2-(3',5'-dibenzyl-2'-hydroxyphenyl)-5-bromobenzotriazole, 2-(3',5'-dibenzyl-2'-hydroxyphenyl)-5-fluorobenzotriazole, 2-(3',5'-di-tert-butyl-2',6'-dihydroxyphenyl)-5-chlorobenzotriazole, 2-(3',5'-di-tert-butyl-2',6'-dihydroxyphenyl)-5-bromobenzotriazole, 2-(3',5'-di-tert-butyl-2',6'-dihydroxyphenyl)-5-fluorobenzotriazole, and mixtures thereof. The presently preferred halo-substituted hydroxyphenylbenzotriazole derivatives are 2-(3',5'-di-tert-butyl-2'-hydroxyphenyl)-5-chlorobenzo-triazole, 2-(3',5'-di-tert-butyl-2'-hydroxyphenyl )-5-bromobenzotriazole, 2-(3',5'-di-tert-butyl-2'-hydroxyphenyl)-5-fluorobenzotriazole, and mixtures thereof. The 2-(3',5'-di-tert-butyl-2'-hydroxyphenyl)-5-chlorobenzotriazole derivative is readily available from Ciba-Geigy under the tradename of Tinuvin 327.

The sulfur-containing aromatic compound suitable for the invention is selected from the group consisting of a thiophenolic compound having the formula of $X_n$—Ar—SH and a thiophenolate having the formula of $X_n$—Ar—SM; the X substituent is selected from the group consisting of hydrogen, chlorine, bromine, iodine, fluorine, cyano, alkyl, alkenyl, phenyl group, biphenyl group, arylthio, amine, ketone, aidehyde, hydroxy, alkoxy, carboxylic acid group, oligomer, and combinations thereof; each X, if it is a carbon-containing substituent, can have 1 to abut 20 carbon atoms; n is a whole number from 1 to 5; Ar is an arylene group; if $n \geq 2$, each X can be the same or different and can be at any available position of the arylene ring; and M is an alkali metal selected from the group consisting of lithium, sodium, potassium, cesium, and mixtures thereof. Examples of the presently preferred sulfur-containing aromatic compound include, but are not limited to, thiophenol, sodium thiophenolate, 4-chlorothiophenol, 3-chlorothiophenol, 4-bromothiophenol, 4-aminothiophenol, 4-cyanothiophenol, 4-ethoxythiophenol, 4-hydroxythiophenol, 2-aminothiophenol, 2-ethoxythiophenol, 2-methoxythiophenol, and mixtures thereof. The presently most preferred sulfur-containing aromatic compound is thiophenol because of its ready availability.

The polar organic compound suitable for use in the present invention will generally substantially dissolve the reactants under the reaction conditions. Representative examples of suitable classes of the polar organic compounds include amides, lactams, sulfones, and mixtures thereof. Specific examples of such polar organic compounds are hexamethylphosphoramide, tetramethylurea, N,N'-ethylene dipyrrolidone, N-methyl-2-pyrrolidone, pyrrolidone, caprolactam, N-ethylcaprolactam, sulfolane, dimethylacetamide, low molecular weight polyamides, and mixtures thereof. The presently most preferred polar organic compound is N-methyl-2-pyrrolidone because of its ease of use and ready availability.

The process of the invention can also be carried out in the presence of a basic compound and/or water. The basic compound used in the invention can be an organic base or an inorganic base and can be in either an aqueous or non-aqueous form. The presently preferred basic compound is an inorganic base. Examples of basic compounds include, but are not limited to, tetramethylammonium hydroxide, potassium hydroxide, sodium hydroxide, lithium hydroxide, magnesium hydroxide, calcium hydroxide, ammonium hydroxide, lithium carbonate, sodium carbonate, potassium carbonate, calcium carbonate, magnesium carbonate, and mixtures thereof. The presently most preferred basic compounds are sodium hydroxide and sodium carbonate because of their availability and ease of use.

The molar ratio of the sulfur-containing aromatic compound to the halo-substituted hydroxyphenylbenzotriazole derivative can vary from about 0.5:1 to about 4:1, preferably about 1:1 for a monohalo-substituted hydroxyphenylbenzotriazole derivative and about 2:1 for a dihalo-substituted hydroxyphenylbenzotriazole derivative. The molar ratio of the polar organic compound to the halo-substituted hydroxyphenylbenzotriazole derivative is in the range of from about 0.1:1 to about 100:1, preferably from 0.5:1 to 20:1. The molar ratio of the basic compound, if present, to the halo-substituted hydroxyphenylbenzotriazole derivative is in the same range as that of sulfur-containing aromatic compound to halo-substituted hydroxyphenylbenzotriazole derivative. The molar ratio of water (if present) to the halo-substituted benzotriazole derivative can be in the range of from about 0.0001:1 to about 20:1.

The aryl sulfide derivative of hydroxyphenylbenzotriazole synthesized by the first step of the invention can be recovered for use as an ultraviolet light stabilizer for polymers. It can also be used as a starting material for the synthesis of an aryl sulfoxide derivative of hydroxyphenylbenzotriazole, an aryl sulfone derivative of hydroxyphenylbenzotriazole, or mixtures of the aryl sulfoxide derivatives of hydroxyphenylbenzotriazole and aryl sulfone derivatives of hydroxyphenylbenzotriazole in the second step of the third embodiment of the invention.

In the second step of the third embodiment of the invention, the aryl sulfide derivative of hydroxyphenylbenzotriazole is contacted with an oxidizing agent under conditions sufficient to oxidize an aryl sulfide derivative of hydroxyphenylbenzotriazole to an aryl sulfoxide derivative of hydroxyphenylbenzotriazole, or an aryl sulfone derivative of hydroxyphenylbenzotriazole, or mixtures thereof. A variation of reaction conditions such as, for example, reaction time, pressure and temperature or oxidizing agents can be used to obtain different sulfur-containing derivatives of hydroxyphenylbenzotriazole.

Any oxidizing agent can be used in the oxidation of the aryl sulfide derivative of hydroxyphenylbenzotriazole. Suitable oxidizing agents include, but are not limited to, hydrogen peroxide, peracetic acid, oxides of nitrogen, sodium peroxide, benzoyl peroxide, chlorine dioxide, m-chloroperbenzoic acid, m-bromoperbenzoic acid, p-chloroperbenzoic acid. In addition, an oxygen-containing fluid such as, for example, oxygen and air, also can be used in the second step of the third embodiment of the invention. The presently preferred oxidizing agents are m-chloroperbenzoic acid and hydrogen peroxide because of their low cost and availability.

Optionally, a catalyst can be employed to promote the oxidation. Suitable catalysts include, but are not limited to tungsten, molybdenum, vanadium, oxides thereof, and mixtures thereof. Specific examples of suitable catlaysts include, but are not limited to tungstic acid, vanadium oxide, vanadium(III) oxide, vanadium(V) oxide, tungsten(VI) oxide, tungsten, mo lybdenum, vanadium, and mixtures thereof.

The oxidation step also can be carried out in the presence of a solvent. The solvent, if employed, should be capable of substantially solubilizing the reactant and the oxidizing agent to improve the reaction. Examples of suitable solvents include, but are not limited to, tetrahydrofuran, carbon tetrachloride, methylene chloride, methanol, ethanol, isopropyl alcohol, propanol, and mixtures thereof. The presently preferred solvent is methylene chloride for it is easy to recover and recycle.

The molar ratio of the oxidizing agent to the aryl sulfide derivative of hydroxyphenylbenzotriazole is in the range of from about 1:1 to about 20:1, preferably from 1:1 to 10:1. The molar ratio of the solvent, if present, to the aryl sulfide derivative of hydroxyphenylbenzotriazole is in the range of from about 10:1 to about 1000:1, preferably from 20:1 to 200:1.

The process of synthesizing a sulfur-containing derivative of hydroxyphenylbenzotriazole can be conducted in any suitable reaction vessel over a wide temperature range, pressure range and time range. The choice of a suitable reaction vessel is a matter of preference to one skilled in the art. The selection of temperature, pressure, and time ranges for optimum results generally depends on the nature of the starting material, the nature of desired products, the oxidizing agent employed, and the solvent used. Broadly the temperature can be as low as 5° C. and as high as 500° C. A preferred temperature in the first step of the process is in the range of from about 100° C. to about 350° C., most preferably 150° C. to 300° C. and that in the second step is in the range of from about 10° C. to about 150° C., most preferably from 15° C. to 90° C.

Broadly the operating pressure can be from slightly below atmospheric to 300 atmospheres. It is however preferred the pressure be in the range of from about 1 atmosphere to about 30 atmospheres, most preferably 1 atmosphere to 15 atmospheres.

The time required for the synthesis of the sulfur-containing derivative of hydroxyphenylbenzotriazole also can be varied from as short as at least about 1 minute to as long as about 25 hours, preferably about 1 minute to about 20 hours, most preferably 10 minutes to 15 hours for each step of the third embodiment of the invention.

The sulfur-containing derivative of hydroxyphenylbenzotriazole can be recovered, if desired, from the reaction mixture by conventional means such as solvent extraction, phase separation, crystallization followed by filtration, and other recovery means.

According to the fourth embodiment of the invention, a UV light-stable composition is provided which comprises a polymer chemically bonded to a sulfur-containing derivative of hydroxyphenylbenzotriazole. The scopes of applicable polymers and sulfur-containing derivatives of hydroxyphenylbenzotriazole are the same as those disclosed previously in the second embodiment of the invention.

Examples of the presently preferred composition comprising a polymer chemically bonded to a sulfur-containing derivative of hydroxyphenylbenzotriazole include, but are not limited to, 2-(3',5'-di-tert-butyl-2'-hydroxyphenyl)-5-(4''-poly(phenylene sulfide)phenylthio)benzotriazole, 2-(3',5'-di-tert-butyl-2'-hydroxyphenyl)-5-(4''-poly(phenylene sulfide)phenylsulfinyl)benzotriazole, 2-(3',5' -di-tert-butyl-2'-hydroxyphenyl)-5-(4''-poly(phenylene sulfide)phenylsulfonyl)benzotriazole, 2-(2'-hydroxyphenyl) -5-(2''-poly(phenylene sulfide)phenylthio)benzotriazole, 2-(2'-hydroxyphenyl)-5-(2''-poly(phenylene sulfide)phenylsulfinyl)benzotriazole, 2-(2'-hydroxyphenyl)-5-(2''-poly(phenylene sulfide)phenylsulfonyl)benzotriazole, 2-(3',5'-di-tert-butyl-2'-hydroxyphenyl) -5-(3''-poly(phenylene sulfide)phenylthio)benzotriazole, 2-(3',5'-di-tert-butyl-2'-hydroxyphenyl)-5-(3''-poly(phenylene sulfide)phenylsulfinyl)benzotriazole, 2-(3',5'-di-tert-butyl-2'-hydroxyphenyl)-5-(3''-poly(phenylene sulfide)phenylsulfonyl)benzotriazole, 2-(2'-hydroxyphenyl)-5-(4''-poly(phenylene sulfide)phenylthio)benzotriazole, 2-(2'-hydroxyphenyl)-5-(4''-poly(phenylene sulfide)phenylsulfinyl)benzotriazole, 2-(2'-hydroxyphenyl)-5-(4''-poly(phenylene sulfide)phenylsulfonyl)benzotriazole, 2-(3',5'-di-tert-butyl-2'-hydroxyphenyl)-5-(3'',4''-dipoly(phenylene sulfide)phenylthio)benzotriazole, 2-(3',5'-di-tert-butyl-2'-hydroxyphenyl)-5-(3'',4''-dipoly(phenylene sulfide)phenylsulfinyl)benzotriazole, 2-(3',5'-di-tert-butyl-2'-hydroxyphenyl) -5-(3'',4''-dipoly(phenylene sulfide)phenylsulfonyl)benzotriazole, 2-(2'-hydroxyphenyl)-5-(2'',4''-dipoly(phenylene sulfide)phenylthio)benzotriazole, 2-(2'-hydroxyphenyl)-5-(2'',4''-dipoly(phenylene sulfide)phenylsulfinyl)benzotriazole, 2-(2'-hydroxyphenyl)-5-(2'',4''-poly(phenylene sulfide)phenylsulfonyl)benzotriazole, 2-(3',5'-di-tert-butyl-2'-hydroxyphenyl)-5-(4"-poly(phenylene sulfide sulfone)phenylthio)benzotriazole, 2-(3',5'-di-tert-butyl-2'-hydroxyphenyl)-5-(4"-poly(phenylene sulfide sulfone)phenylsulfinyl)benzotriazole, 2-(3',5'-di-tert-butyl-2'-hydroxyphenyl)-5-(4"-poly(phenylene sulfide sulfone)phenylsulfonyl)benzotriazole, 2-(2'-hydroxyphenyl)-5-(2"-poly(phenylene sulfide sulfone)phenylthio)benzotriazole, 2-(2'-hydroxyphenyl)-5-(2"-poly(phenylene sulfide sulfone)phenylsulfinyl)benzotriazole, 2-(2'-hydroxyphenyl)-5-(2"-poly(phenylene sulfide sulfone)phenylsulfonyl)benzotriazole, 2-(3',5'-di-tert-butyl-2'-hydroxyphenyl)-5-(4"-poly(phenylene oxide)phenylthio)benzotriazole, 2-(3',5'-di-tert-butyl-2'-hydroxyphenyl)-5-(4"-poly(phenylene oxide)phenylsulfinyl)benzotriazole, 2-(3',5'-di-tert-butyl-2'-hydroxyphenyl)-5-(4"-poly(phenylene oxide)phenylsulfonyl)benzotriazole, 2-(2'-hydroxyphenyl)-5-(2"-poly(phenylene oxide)phenylthio)benzotriazole, 2-(2'-hydroxyphenyl)-5-(2"-poly(phenylene oxide)phenylsulfinyl)benzotriazole, 2-(2'-hydroxyphenyl)-5-(2"-poly(phenylene oxide)phenylsulfonyl)benzotriazole, and mixtures thereof. The presently most preferred compositions are 2-(3',5'-di-tert-butyl-2'-hydroxyphenyl)-5-(4"-poly(phenylene sulfide)phenylthio)benzotriazole, 2-(3',5'-di-tert-butyl-2'-hydroxyphenyl)-5-(4"-poly(phenylene sulfide)phenylsulfinyl)benzotriazole, 2-(3',5'-di-tert-butyl-2'-hydroxyphenyl)-5-(4"-poly(phenylene sulfide)phenylsulfonyl)benzotriazole, and mixtures thereof.

The amount of sulfur-containing derivative of hydroxyphenylbenzotriazole that is present in the composition is in the range of from about 0.0001 to about 5 moles, preferably from about 0.001 to about 2 moles, and most preferably from 0. 002 to 1.0 moles, per 100 repeat units of the polymer, or per gram-atom of sulfur which is present in sulfur-containing polymers such as, for example, poly(arylene sulfide).

The preparation of the compositions of the fourth embodiment of the invention is disclosed hereinbelow in the fifth embodiment of the invention.

In the fifth embodiment of the invention, the composition disclosed in the fourth embodiment of the invention is prepared by contacting a halo-substituted sulfur-containing derivative of hydroxyphenylbenzotriazole with a reaction mixture comprising a sulfur source and at least one halogen-containing aromatic monomer in a polar organic compound under polymerization conditions to synthesize the polymer. The term monomer is used herein, unless otherwise indicated, to generically mean monomers, comonomers, termonomers, etc.

The halo-substituted sulfur-containing derivative of hydroxyphenylbenzotriazole can be represented by the formula of:

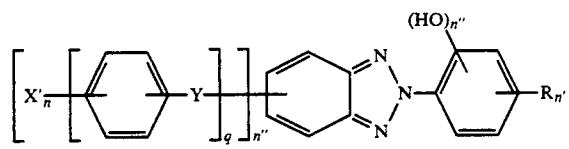

wherein each X' is a chlorine, bromine, iodine, fluorine or a suitable leaving group capable of being substituted by the sulfur-containing aromatic compound; n is a whole number from 1 to 5; n' is an integer from 0 to 4; n" is an integer from 1 to 2 and each n" can be the same or different; q is an integer of 1 to 10; and each Y is selected from the group consisting of —S(O)(O)—, —S—, and combinations thereof; each R can be the same or different and each can be selected from the group consisting of hydrogen, alkyl group, alkenyl group, an aralkyl group, an alkaryl group and mixtures thereof; each R can have 0 to about 10 carbon atoms; and when R has more than 2 carbon atoms, it can be linear, branched or cyclic; each OH group can be at the 2'- or the 6'-position, or both. Additionally, X', Y and R can be at any available position of the arylene rings. The preferred halo-substituted sulfur-containing derivative of hydroxyphenylbenzotriazole is selected from the group consisting of 2-(3'-5'-di-tert-butyl-2'-hydroxylphenyl)-5-(4"-iodophenylthio)benzotriazole, 2-(3',5'-di-tert-butyl-2'-hydroxylphenyl)-5-(4"-iodophenylsulfonyl)benzotriazole, 2-(3',5'-di-tert-butyl-2'-hydroxyphenyl)-5-(4"-chlorophenylthio)benzotriazole, 2-(3'-5'-di-tert-butyl-2'-hydroxyphenyl)-5-(4"-chlorophenylsulfonyl)benzotriazole, 2-(2'-hydroxyphenyl)5-(4"-bromophenylthio)benzotriazole, 2-(2'-hydroxyphenyl)-5-(4"-bromophenylsulfonyl)benzotriazole, 2-(3',5'-di-tert-butyl-2'-hydroxylphenyl)-5-(4"-bromophenylthio)benzotriazole, 2-(3',5'-di-tert-butyl-2'-hydroxylphenyl)-5-(4"-bromophenylsulfonyl)benzotriazole, and mixtures thereof. Other sulfur-containing derivatives of hydroxyphenylbenzotriazole disclosed in the previous embodiments of the invention can be reacted with a halogen in a solvent to prepare these preferred halo-substituted sulfur-containing derivatives of hydroxyphenylbenzotriazole. The molar ratio of halogen to the other sulfur-containing derivatives of hydroxyphenylbenzotriazole is in the range of from about 0.1:1 to about 10:1, preferably from 0.5:1 to 2:1. Examples of the presently preferred solvent include, but are not limited to, carbon tetrachloride, chloroform, methylene chloride, N-methyl-2-pyrrolidone, tetrahydrofuran, sulfolane, and mixtures thereof. The presently most preferred solvent is carbon tetrachloride. The molar ratio of the solvent to the other sulfur-containing derivatives of hydroxyphenylbenzotriazole can vary widely from about 10:1 to about 5000:1, preferably from 50:1 to 1000:1. The reaction conditions can also vary widely, preferably in a temperature range of from about −10° C. to about 80° C., preferably 0° C. to 50° C. for about 1 hour to about 15 days under a pressure range of from about 1 atmosphere to about 5 atmospheres, preferably about 1 atmosphere.

The presently preferred sulfur source is selected from the group consisting of alkali metal sulfides, alkali metal hydrosulfides, thiosulfates, thioureas, thioamides, and mixtures of any two or more thereof. Examples of the presently preferred sulfur source include, but are not limited to, sodium sulfide, sodium hydrosulfide, potassium sulfide, potassium hydrosulfide, lithium thiosulfate, sodium thiosulfate, potassium thiosulfate, rubidium thiosulfate, 1-methyl-2-thiourea, 1,3-diisopropyl-2-thiourea, 1-p-tolyl-2-thiourea, thioacetamide, 2-thiopyrrolidone, and mixtures of any two or more thereof. The presently most preferred sulfur sources are sodium sulfide and sodium hydrosulfide because of availability and low cost.

The presently preferred halogen-containing aromatic monomer is a p-dihalobenzene having the formula of:

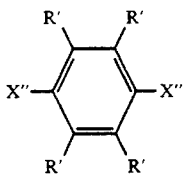

where each X" is selected from the group consisting of fluorine chlorine, bromine, and iodine, and each R' is selected from the group consisting of hydrogen and hydrocarbyl radical in which the hydrocarbyl radical can be alkyl, cycloalkyl, and aryl radicals and combinations thereof such as, for example alkaryl, and aralkyl, and the like, the total number of carbon atoms in each molecule being within the range of 6 to about 24.

Examples of some p-dihalobenzenes which can be employed in the process of this invention include p-dichlorobenzene, p-dibromobenzene, p-diiodobenzene, 1-chloro-4-bromobenzene, 1-chloro-4-iodobenzene, 1-bromo-4-iodobenzene, 2,5-dichlorotoluene, 2,5-dichloro-p-xylene, 1-ethyl-4-isopropyl-2,5-dibromobenzene, 1,2,4,5-tetramethyl-3,6-dichlorobenzene, 1-butyl-4-cyclohexyl-2,5-dibromobenzene, 1-hexyl-3-dodecyl-2,5-dichlorobenzene, 1-octadecyl-2,5-diiodobenzene, 1-phenyl-2-chloro-5-bromobenzene, 1-p-tolyl-2,5-dibromobenzene, 1-benzyl-2,5-dichlorobenzene, 1-octyl-4-(3-methylcyclopentyl)-2,5-dichlorobenzene, and mixtures thereof.

The scope of the polar organic compound suitable for the fifth embodiment of the invention is the same as that for the third embodiment of the invention described above.

A basic compound also can be present in the polymerization reaction of the fifth embodiment of the invention. The scope of the basic compound is the same as that disclosed for the third embodiment of the invention.

The process of the present invention can also be carried out by contacting metal carboxylate with the reactants described above to modify the molecular weight of the resulting copolymers. It can also be carried out in the presence of water. The metal carboxylate has the formula of R'CO$_2$M where M is a metal selected from the group consisting of alkali metals and alkaline earth metals and R' is a hydrocarbyl radical selected from the group consisting of alkyl, cycloalkyl, aryl, alkenyl, and mixtures of any two or more thereof. Preferably R' is an alkyl radical having 1 to about 6 carbon atoms or a phenyl radical and M is lithium or sodium. If desired, the metal carboxylate can be employed as a hydrate or as a solution or dispersion in water.

Examples of some metal carboxylates which can be employed in the process of this invention include, but are not limited to, lithium acetate, sodium acetate, potassium acetate, lithium propionate, sodium propionate, lithium 2-methylpropionate, rubidium butyrate, lithium valerate, sodium valerate, cesium hexanoate, lithium heptanoate, lithium 2-methyloctanoate, potassium dodecanoate, rubidium 4-ethyltetradecanoate, sodium octadecanoate, lithium cyclohexanecarboxylate, cesium cyclododecanecarboxylate, sodium 3-methylcyclopentanecarboxylate, potassium cyclohexylacetate, potassium benzoate, lithium benzoate, sodium benzoate, potassium m-toluate, lithium phenylacetate, sodium 4-phenylcyclohexanecarboxylate, potassium p-tolylacetate, lithium 4-ethylcyclohexylacetate, and mixtures of any two or more thereof.

According to the fifth embodiment of the present invention, the contacting of the above described reactants can take place in the presence of water. Water can also be formed from the interaction of certain sulfur sources and alkali metal hydroxides, if employed.

According to the fifth embodiment of the present invention, at least one halogen-containing aromatic compound, a sulfur source, a halo-substituted sulfur-containing derivative of hydroxyphenylbenzotriazole, a polar organic compound, and optionally compounds selected from the group consisting of a base, an alkali metal carboxylate, a water source and mixtures thereof, are contacted in a suitable reactor to form a polymerization mixture. The choice of a suitable reactor is a matter of preference to one skilled in the art. The polymerization mixture then can be subjected to suitable polymerization conditions. Suitable polymerization conditions can vary widely and generally include a temperature in the range of from about 100° C. to about 400° C., preferably about 150° C. to about 350° C., most preferably from 180° C. to 280° C., and a time of from about 5 minutes to about 80 hours, preferably from about 10 minutes to about 70 hours, most preferably from 1 hour to 30 hours. The pressure employed is not critical, although it is preferred that the pressure be sufficient to maintain the polymerization reactants substantially in the liquid phase.

The halo-substituted sulfur-containing derivative of hydroxyphenylbenzotriazole may be present at the beginning of the polymerization or may be added at any time during the polymerization. Alternatively, the polymerized resin may be treated with the halo-substituted sulfur-containing derivative of hydroxyphenylbenzotriazole and a sulfur source under suitable polymerization conditions.

The molar ratio of reactants can vary considerably. However, the molar ratio of the halogen-containing aromatic monomer to the sulfur source is preferably from about 0.95:1 to about 1.20:1, most preferably from 0.99:1 to 1.05:1 for best results.

If an alkali metal hydroxide is employed with a suitable sulfur source, the amount of alkali metal hydroxide to the sulfur source will vary according to the sulfur source but generally will be from about 0.001 to about 5 and preferably 0.001 to 4 gram equivalents per gram-atom of sulfur in the sulfur source.

If at least one alkali metal carboxylate is employed according to the invention, the molar ratio of alkali metal carboxylate to the sulfur source is generally about 0.001:1 to about 1.5:1 and preferably about 0.01:1 to about 1:1 to provide a polymer composition with desirable molecular weight.

The amount of polar organic compound employed according to the invention can be expressed in terms of a molar ratio of polar organic compound to the sulfur source. Generally, this ratio is about 2:1 to about 25:1 and preferably about 2:1 to about 15:1 so that the reactants will be substantially in a liquid state.

The process of the present invention can be conducted by various methods including batch and continuous processes. One method is to admix the reactants described in a suitable reactor under the conditions described above.

The composition produced according to the present invention can be separated from the final polymerization reaction mixture by conventional procedures, for example by filtration of the polymerization reaction mixture to separate the composition therefrom, followed by washing with water. Alternatively, the heated polymerization reaction mixture can be diluted with water or additional polar organic compound or a mixture thereof followed by cooling and filtration and water washing of the polymer. Preferably, at least a portion of the water washing is conducted at an elevated temperature, e.g. within the range of from about 30° C. to about 100° C., preferably from 50° C. to 95° C.

The polymer compositions produced by the process of the fifth embodiment of the invention can be blended with poly(phenylene sulfide)s, fillers, pigments, extenders, other polymers, and the like. They can be cured through crosslinking and/or chain extension by heating at temperatures up to about 480 ° C., in the presence of a free oxygen-containing gas, to provide cured products having high thermal stability and good chemical resistance. They are useful in the production of coatings, film, molded objects, and fibers.

The following examples are provided to merely illustrate and are not intended to limit the scope of the present invention.

Example I

This example illustrates the synthesis of 2-(3',5'-di-tert-butyl-2'-hydroxyphenyl)-5-(phenylthio)benzotriazole.

The run was carried out in a 300 ml autoclave equipped with a mechanical stirrer and an overhead condenser. Thiophenol (11.55 g; 0.105 mol), 4.20 g (0.105 mol) sodium hydroxide, 5.0 g (0.280 mol) water, and 90.0 g (0.908 mol) N-methyl-2-pyrrolidone (hereinafter referred to as NMP) was charged to the 300 ml autoclave which was then sealed and purged with 50 psi argon three times. Subsequent dehydration of the reaction mixture was carried out by slowly increasing the autoclave temperature from 150° C. to 200° C. and allowing water to distill out through the condenser. Approximately 7.0 g of distillate was collected. The reaction mixture was allowed to cool to 25° C., after which the autoclave top was removed and 35.97 g (0.10 mol) 2-(3',5'-di-tert-butyl-2'-hydroxyphenyl)-5-chlorobenzotriazole (obtained from Ciba-Geigy Corp.) and 60.0 g (0,605 mol) NMP was added. The reactor was then resealed, repurged with argon, and heated to 200° C. for 6 hours.

After cooling to 25° C., the heterogeneous reaction mixture (i.e., a mixture of solvent and precipitated product) was worked up by transferring the mixture from the autoclave with 200 ml of water and further diluting it (50/50 by volume) with a 50% aqueous solution of HCl. The acidified mixture (pH=1) was extracted three times with methylene chloride (400 ml). Recrystallization from the methylene chloride extract was achieved by first heating the extraction solvent to boiling followed by the slow addition of a 15% water/methanol solution (200 ml) until the solution retained a slight haze (occurs at about a 50/50 dilution). The solution was then allowed to cool to 25° C. after which it was placed in an ice bath (4° C.) for 2.5 hours. The resulting yellow, needle-like crystals were collected by suction filtration, washed with methanol (100 ml), and dried in a vacuum (25 torr) oven for 3 hours at 100° C. The yield of this product was 32.93 g (76.2%). This product melts at 133° C. to 134° C. and is >99% pure by gas chromatography. Mass spectroscopy and carbon-13 NMR spectrometry of this product showed it to be 2-(3',5'-di-tert-butyl-2'-hydroxyphenyl)-5-(phenylthio)benzotriazole.

EXAMPLE II

This example illustrates the synthesis of 2-(3',5'-di-tert-butyl-2'-hydroxyphenyl)-5-(phenylsulfonyl)benzotriazole.

The 2-(3',5'-di-tert-butyl-2'-hydroxyphenyl)-5-(phenylthio)benzotriazole (5.0 g; 0.012 mol) synthesized in Example I was dissolved in 50 g of methylene chloride in a 300 ml flask which was cooled on an ice bath at 4° C. A magnetic stirring bar was used to mix the contents of the flask. With stirring, 8.2 g (2 equivalents of 50% reagent) of m-chloroperbenzoic acid in 150 g methylene chloride was added slowly over a period of about 30 minutes to the 2-(3',5'-di-tert-butyl-2'-hydroxyphenyl)-5-(phenylthio)benzotriazole solution under a nitrogen gas flow.

The reaction mixture was stirred under nitrogen for 3 hours at 25° C. Thereafter, precipitated solids were removed from the resulting reaction mixture by filtration. After an additional rinse of the solids with methylene chloride, the solids were discarded. The filtrates were combined, washed twice with a saturated solution of $NaHCO_3$ solution (100 ml each wash), and subjected to rotary evaporation. The residue was then recrystallized from ethanol/$H_2O$ (volumetric ratio 80/20). The product was recovered and dried as described in Example I. The product yield was 4.87 g. Instrumental analyses (as described in Example I) showed it was 2-(3',5'-di-tert-butyl-2'-hydroxyphenyl)-5-(phenylsulfonyl)benzotriazole.

EXAMPLE III

This example illustrates the synthesis of a mixture of 2-(3',5'-di-tert-butyl-2'-hydroxyphenyl)-5-(phenylsulfinyl)benzotriazole and 2-(3',5'-di-tert-butyl-2'-hydroxyphenyl)-5-(phenylsulfonyl)benzotriazole by a catalytic oxidation of 2-(3',5'-di-tert-butyl-2'-hydroxyphenyl)-5-(phenylthio)benzotriazole.

The starting sulfide precursor 2-(3',5'-di-tert-butyl-2'-hydroxyphenyl)-5-(phenythio)benzotriazole (21.53 g) was stirred with 78.5 g of 2-propanol and 0.1 g of tungstic acid in a 300 ml 3-necked round-bottom flask under nitrogen. The reaction mixture was then heated to 80° C. and 22.2 g of hydrogen peroxide was added slowly (over 1 hour).

The reaction was allowed to react at 80° C. for 12 hours. After this time the reaction mixture was filtered. The filtered solid was washed with 39.25 g of 2-propanol followed by 100 g of water and dried at 80° C. under vacuum (1 torr) for 24 hours. A yellow solid (19.18 g) was recovered after drying. Analysis of the product by GC showed it to be 94.0 wt % 2-(3',5'-di-tert-butyl-2'-hydroxyphenyl)-5-(phenylsulfonyl)benzotriazole, 4.6 wt % 2-(3',5'-di-tert-butyl-2'-hydroxyphenyl)-5 -(phenylsulfinyl)benzotriazole, and 0.8 wt % unreacted 2-(3',5'-di-tert-butyl-2'-hydroxyphenyl)-5-(phenythio)benzotriazole.

EXAMPLE IV

This example illustrates the manifestation of UV-induced photodegradation of poly(phenylene sulfide).

A. Poly(phenylene sulfide) (hereinafter referred to as PPS) is commercially available from Phillips Petroleum Company, Bartlesville, Okla.

B. Film Preparation—PPS films were made directly from pellets, powder, or small chunks of the resin. A heat/press molding technique was used for preparing films. A weighed amount (2.7–3.0 g) of the resin (pellets, chunks, or powder) was placed between two 8"×8" Kapton sheets (2 mil) interspaced by a square frame, also made from a 2 mil Kapton sheet. The inner open space of the frame was 7"×7", and was meant to be filled by the resin in the course of melting and compression. The Kapton sheets with the resin placed in between them were clamped together between two steel plates and the resulting assembly was then placed in a hot press maintained at 320° C. With the clamping force maintained between 1,000–2,000 pounds (16–32 psig) for 3 minutes, the resin was allowed to melt and distribute itself in the space available between the Kapton sheets. The clamping force was then raised to 35,000 pounds (550 psig) and maintained at that value for 3 minutes. Finally, the hot plate/sheet assembly was quickly removed from the hot press (following the release of the clamping force) and inserted between the platens of a cold press (maintained at 15°–20° C. by constant circulation of a cold tap water through internal coils). The clamping force of the cold press was raised to 35,000 pounds (550 psig) as soon as practicable and maintained there for 2.5–3.0 minutes. This rapid cooling technique was suited to making amorphous films.

In a few cases, the films ended up being predominantly crystalline in spite of rapid cooling. In such cases, amorphous films were obtained by quickly dipping the hot plate/sheet assembly in ice water baths. The films prepared in this manner were characterized by slightly kinked (wavy) surfaces and tiny bubble-like blemishes in the bulk.

C. Irradiation Conditions—All of the photocoloration tests were done by use of Xe-arc Weather-Ometers as irradiation sources. Two Atlas Weather-Ometers (models 600-W and Cl-35W) were used, but the bulk of the work was based on model 600-W. Both were equipped with high-pressure, 5000 W, Xe lamps with borosilicate filters; the latter absorbed the deep UV portion of the lamp output and made available only the light in near UV and visible regions. The intensities of the lamps were maintained at 0.55 watt/m² (at 340 nm).

D. Color Change (ΔE) Measurements—A Hunter colorimeter, model D25 OPTICAL SENSOR, was used in the reflection mode to determine film colors. Color values, as measured in a Hunter colorimeter which simulates the tristimulus response to human eyes, were resolved into three components, namely, the lightness (L), green-to-red (a) and blue-to-yellow (b) scales. On the L-scale, the values of 100 and 0 correspond to white and black, respectively (gray=50). On the a-scale, a change from negative to positive values means a change from green to red (gray=0), and a similar change on the b-scale denotes going from blue to yellow (gray=0), The overall color change (ΔE) experienced by a PPS film upon UV exposure was calculated from the individual color values for the film before and after exposure using the following equation:

$$\Delta E = (\Delta L^2 + \Delta a^2 + \Delta b^2)^{\frac{1}{2}}$$

The color changes occurring upon UV exposure for films made from two commercial fiber-grade PPS resins, PPS A and PPS B (both are available from Phillips Petroleum Company, Bartlesville, Okla.), are shown in Table I.

TABLE I

Detailed Color Changes of Representative PPS Films

| Film | Before Irradiation | | | After 50 h Irradiation in Weather-Ometer | | | | | | |
|---|---|---|---|---|---|---|---|---|---|---|
| | L | a | b | L | a | b | ΔL | Δa | Δb | ΔE |
| PPS A | 84.09 | −1.36 | 6.91 | 70.75 | 0.38 | 23.91 | −13.34 | 1.74 | 17.00 | 21.7 |
| PPS B | 87.47 | −1.38 | 5.24 | 75.33 | −1.10 | 20.34 | −12.14 | 0.28 | 15.10 | 19.4 |

Table I shows that the color change for PPS B was slightly lower than that for PPS A. The major contributions to the overall color changes (ΔE) for both films came from a decrease of L (i.e., graying) and an increase in b (i.e., yellowing). The changes in the a-scale were insignificant. It should also be noted that a ΔE value of less than 2 is imperceptible to the human eye.

Minor fluctuations in color change values were caused by lamp intensity variations in the Weather-Ometers. For PPS films, color changes were therefore normalized by comparisons to those of standard PPS films included as controls in every test. In order to avoid confusion the common practice was to include films as controls in every batch and normalize the observed ΔE values of experimental films so that the ΔE for the control was always about 20 units.

EXAMPLE V

This example shows that different post polymerization treatments and film preparation techniques had little or no effect on PPS photodegradation behavior.

The tests for photodegradation were carried out the same as those described in Example IV.

Post-Polymerization Treatments—Films made from PPS resins that had been given the various treatments shown in Table II were exposed to UV light as described in Example IV.C. The ΔE values given in Table II show no significant differences. The data in Table II demonstrate that the indicated post-polymerization treatments of PPS had little or no effect on photodegradation of PPS films.

TABLE II

Photocolorations of Treated Resin

| Run | Wash[a] | ΔE |
|---|---|---|
| 1 | Water | 19.5 |
| 2 | Water | 20.5 |
| 3 | Aqueous acetic acid | 18.6 |
| 4 | Aqueous calcium acetate | 21.8 |

[a]Resin (PPS A, Table I) was treated as shown after recovery from polymerization mixture.

Film Thickness—Almost all of the photoinduced color change runs were done with PPS films having thicknesses close to 2 mil. It was of interest to determine if the Hunter color parameters (L, a, b) for PPS films and their changes upon UV irradiation of the films were sensitive to the film thicknesses. Table III shows data for films with thicknesses in the range of 2–6 mils. The ΔE's were essentially independent of film thickness, in spite of the fact that the thickest film (6 mil) in this set was a little darker (i.e., possessed a relatively low, initial L value).

TABLE III

Effect of Film Thickness on Photocoloration of PPS A Films

| Thickness (mil) | Before Irradiation | | | After 50 h Irradiation in Weather-Ometer | | | | | | |
|---|---|---|---|---|---|---|---|---|---|---|
| | L | a | b | L | a | b | ΔL | Δa | Δb | ΔE |
| 2 | 83.34 | −1.25 | 7.12 | 72.41 | −0.82 | 23.77 | −10.93 | 0.43 | 16.65 | 19.9 |
| 4 | 84.33 | −1.07 | 9.37 | 72.29 | −1.15 | 25.20 | −12.04 | −0.08 | 15.83 | 19.9 |
| 6 | 79.02 | −1.25 | 10.11 | 68.33 | −0.24 | 25.75 | −10.69 | 1.01 | 15.64 | 19.0 |

Resin Purification: Effect of Oligomer Content—The effect of impurities, especially cyclic and linear oligomers that are present to the extent of 3-4 weight % in some commercial PPS resins on photocoloration was also examined. A resin sample, from which the oligomers had been removed by exhaustive Soxhlet extraction with dichloromethane, was subjected to photostability tests following redoping with varying amounts of the extracted oligomers. The UV-induced color changes of the films are given in Table IV. Within experimental error, the oligomers, when added up to 20 wt. %, did not influence ΔE. The individual color components (i.e., L, a, and b parameters) were similarly unaffected.

Tables II to IV show that a variety of treatments of PSS resins did not produce satisfactory results in stabilizing PPS polymers against UV discoloration.

TABLE IV

Effects of Oligomer Content on PPS Photocoloration

| Weight % of Extracted Oligomers Added Back to Solvent-Extracted PPS | ΔE[a] |
|---|---|
| 0.0 | 21.4 ± 0.9 |
| 0.50 | 20.8 ± 1.0 |
| 1.25 | 20.6 ± 1.5 |
| 2.5 | 22.1 ± 0.4 |
| 5.0 | 21.2 ± 1.5 |
| 10.0 | 20.9 ± 1.3 |
| 20.0 | 21.0 ± 0.5 |

[a]After 50 hours irradiation in a Weather-Ometer.

EXAMPLE VI

This example illustrates the effect of sulfur-containing derivatives of hydroxyphenylbenzotriazole of the invention on reducing the photodegradation of PPS by UV irradiation.

PPS resin (3.0 g) was dry blended with sulfur-containing derivatives of hydroxyphenylbenzotriazole in the amounts shown in Table V. Each blend was mixed using a mortar and pestle and was then molded into a film as described in Example IV. The films were used for the photodegradation tests described in Example IV, and the test data are shown in Table V.

TABLE V

UV-induced Color Changes of PPS Films Containing a Sulfur-Containing Derivative of Hydroxyphenylbenzotriazole

| Run No.[a] | Additive | Wt. % | ΔE |
|---|---|---|---|
| 10 | None | — | 21.7 |
| 11 | PTHPBT[b] | 1.1 | 12.5 |
| 12 | PTHPBT | 1.9 | 11.4 |
| 13 | PTHPBT | 3.8 | 9.5 |
| 14 | PTHPBT | 4.6 | 7.6 |
| 15 | PTHPBT | 5.6 | 3.9 |
| 16 | PTHPBT | 7.6 | 4.7 |
| 17 | PTHPBT | 11.0 | 3.7 |
| 18 | PTHPBT | 7.9 | 5.1 |
| 19 | PTHPBT | 7.9 | 4.9 |
| 20 | PSHPBT[c] | 1.1 | 10.8 |
| 21 | PSHPBT | 2.5 | 8.4 |
| 22 | PSHPBT | 4.1 | 5.0 |
| 23 | PSHPBT | 6.1 | 2.7 |
| 24 | PSHPBT | 7.8 | 1.6 |
| 25 | PSHPBT | 11.3 | 1.0 |

[a]The resin used for these runs was PPS A.
[b]PTHPBT = 2-(3',5'-di-tert-butyl-2'-hydroxyphenyl)-5-(phenylthio)-benzotriazole.
[c]PSHPBT = 2-(3',5'-di-tert-butyl-2'-hydroxyphenyl)-5-(phenylsulfonyl)-benzotriazole.

Data presented in Table V show that, with PSHPBT at 8-11% loadings, ΔE's<2 became achievable. Also Thermal Gravimetric Analysis (a test method where a sample's weight loss is followed as its temperature is increased) showed that both of the sulfur-containing derivatives of hydroxyphenylbenzotriazole in Table V are nonvolatile at 310° C. and should therefore be totally retained by the polymer during the hot compression molding operation.

EXAMPLE VII

This example illustrates that the sulfur-containing derivatives of hydroxyphenylbenzotriazole of the invention are also effective photostabilizers for PPS resins that had been treated with aqueous solutions containing cations. The runs were carried out the same as those in Example VI except that the resins were blended with the amounts of sulfur-containing derivatives shown in Table VI. The ΔE data given in Table VI show that at a comparable loading of the same UV-absorber, the cation-laced resins responded less favorably to the photostabilizing action. For example, PPS films with 7.8-11.3 wt. % of PSHPBT consistently gave ΔE's less than 2 (Table V), while PPS films produced from Ca+2-washed resins with PSHPBT in the same wt % range gave ΔE's in the vicinity of 4 (Table VI). Washing of PPS is well-known to those skilled in the art.

TABLE VI

Effect of UV Stabilizers on Photostabilization of Cation-treated PPS Resins

| Run[a] | Additive (wt. %) | ΔE |
|---|---|---|
| 27 | None | 19.4 |
| 28 | None | 20.6 |
| 29 | PSHPBT[b] (2.1) | 9.2 |
| 30 | PSHPBT (4.0) | 5.5 |
| 31 | PSHPBT (7.9) | 3.7 |
| 32 | PSHPBT (11.9) | 3.7 |
| 33 | PSHPBT (8.1) | 4.2 |
| 34 | Tinuvin 327[c] (5.2) | 5.1 |
| 35 | PSHPBT (8.1) | 2.4 |
| 36 | Tinuvin 327 (4.9) | 7.6 |
| 37 | PSHPBT (8.2) | 4.8 |
| 38 | Tinuvin 327 (5.2) | 6.6 |

TABLE VI-continued

Effect of UV Stabilizers on Photostabilization of Cation-treated PPS Resins

| Run[a] | Additive (wt. %) | ΔE |
|---|---|---|
| 39 | PTHPBT[d] (7.8) | 7.4 |

[a]In run 27, the resin was not washed. In runs 28-34 and 39, the resins were washed with aqueous Ca(OH)$_2$. In runs 37-38, the resin was washed with aqueous NaOH. In runs 35-36, the resins were washed with aqueous Zn(OH)$_2$. All initial resins used in this Table were PPS B.
[b]See footnote c, Table V.
[c]Tinuvin 327 is a tradename for 2-(3',5'-di-tert-butyl-2'-hydroxy-phenyl)-5-chlorobenzotriazole which is commercially available from Ciba-Geigy Corporation, Hawthorne, New York.
[d]See footnote b, Table V.

EXAMPLE VIII

This example shows that the mixture of sulfur-containing derivatives of hydroxyphenylbenzotriazole obtained in Example III can be used to stabilize PPS.

The runs were carried out the same as described in Example VI except that the mixture of sulfur-containing derivatives of hydroxyphenylbenzotriazole prepared in Example III was used as the additive. The results are shown in Table VII.

TABLE VII

UV-induced Color Changes of PPS Films Containing a Mixture of Sulfur-containing Derivatives of Hydroxyphenylbenzotriazole[a]

| Wt % of Mixture of Sulfur-containing Derivatives of Hydroxyphenylbenzotriazole in PPS Films | ΔE[b] |
|---|---|
| 0 | 20.0 |
| 2.1 | 5.8 |
| 4.0 | 2.8 |
| 5.9 | 2.2 |
| 8.1 | 1.1 |
| 10.4 | 1.9 |

[a]See Example III.
[b]After 50 hours of irradiation.

As shown in Table VII, films made from the PPS resins containing the mixture of sulfur-containing derivatives of the present invention had much less color change as measured by ΔE after 50 hours of UV irradiation than did the unstabilized PPS films.

EXAMPLE IX

This example is a comparative example illustrating that mixing with commercially available non-sulfur-containing hydroxyphenylbenzotriazole derivatives did not reduce the deleterious effect of UV on PPS as effectively as the sulfur-containing hydroxyphenylbenzotriazole derivatives of the invention shown in Tables V and VII.

The runs were carried out the same as those described in Example VI except that the additives and concentrations thereof are as shown in Table VIII.

TABLE VIII

Effects of Commercial UV Stabilizers on PPS Photostabilization

| Run[a] | Additive | Weight % | ΔE[a] |
|---|---|---|---|
| 22 | PSHPBT[b] | 4.1 | 5.0 |
| 40 | Tinuvin 234[c] | 1.0 | 9.7 |
| 41 | Tinuvin 234 | 2.0 | 7.4 |
| 42 | Tinuvin 234 | 3.0 | 8.1 |
| 43 | Tinuvin 234 | 4.0 | 5.9 |
| 44 | Tinuvin 327[d] | 1.0 | 12.9 |
| 45 | Tinuvin 327 | 2.1 | 9.2 |
| 46 | Tinuvin 327 | 4.0 | 7.5 |
| 47 | Tinuvin 327[e] | 4.0 | 8.2 |
| 48 | Cyasorb 531[f] | 4.1 | 11.4 |
| 49 | None | — | 21.0 |

[a]See footnote a, Table V.
[b]PSHPBT, see footnote c of Table V.
[c]Tinuvin 234 is a tradename for 2-(3',5'-di-(α,α-dimethylbenzyl)-2'-hydroxyphenyl)-benzotriazole commercially available from Ciba-Geigy.
[d]See footnote c, Table VI.
[e]Tinuvin 328 is a tradename for 2-(3',5'-di-tert-amyl-2'-hydroxy-phenyl)benzo-triazole commercially available from Ciba-Geigy.
[f]Cyasorb 531 is 2-hydroxy-4-n-octyloxybenzophenone, commercially available from American Cyanamid.

Table VIII shows that films made from resins mixed with commercially available UV stabilizers at about 4% levels, though reducing the ΔEs, were not as effectively photostabilized as films containing the inventive additives (comparing runs 43, 47, and 48 with run 22). For further comparison purposes, run 48, using a commercial UV stablizer that is not a hydroxyphenylbenzotriazole derivative, was included to show that it was not as effective for PPS photostabilization as the inventive stabilizers (compared to runs in Table V).

EXAMPLE X

This example demonstrates the synthesis of 2-(3',5'-di-tert-butyl-2'-hydroxyphenyl)-5-(4''-bromophenylsulfonyl)benzotriazole. The starting sulfide precursor 2-(3',5'-di-tert-butyl-2'-hydroxyphenyl)-5-(phenythio)-benzotriazole (189.0 g) (Example I) was mixed with 1,195.5 g of carbon tetrachloride under argon. The mixture was then cooled with ice to about 0° C. for 1 hour.

After this time a solution of 79.6 g bromine in 318.8 g carbon tetrachloride was slowly added (over 65 rain) to the cooled mixture. Following the addition of the bromine solution, the reaction mixture was brought to room temperature (25° C.) and stirred for 7 days.

The reaction product was worked up by removing the carbon tetrachloride via. rotary evaporation. The resulting solid was redissolved in carbon tetrachloride (794.0 g), followed by removing the carbon tetrachloride via rotary evaporation. The process was repeated in order to insure the removal of all unreacted bromine. The resulting product was recrystallized from a 50/50 mixture of methylene chloride and a water-ethanol solution (15% water). The recrystallized product (yellow needles) was collected and dried under vacuum (25 torr) at 127° C. overnight.

The dried prdouct (197.17 g) had a melting point of 158°-159° C. and was shown by GC to be >99% pure. Analysis of this product by mass spectroscopy and NMR showed it to be 2-(3',5'-di-tert-butyl-2'-hydroxyphenyl)-5-(4''-bromophenylthio)benzotriazole.

This product was further oxidized by the methods described in Example II to make 2-(3',5'-di-tert-butyl-2'-hydroxyphenyl)-5-(4''-bromophenylsulfonyl)benzotriazole. The identity of this product was confirmed by mass spectroscopy and NMR analysis.

EXAMPLE XI

This example illustrates the synthesis of a polymer composition comprising poly(phenylene sulfide) which is chemically bonded to a sulfur-containing derivative of hydroxyphenylbenzotriazole.

A 1-liter autoclave equipped with a mechanical stirrer and an overhead condenser was charged with sodium hydrosulfide (95.33 g of 58.81% of solution; 1.0 mole), sodium hydroxide (41.57 g; 1.02 mole), NMP (250 g; 2.5 moles) and sodium acetate (24.66 g; 0.3 mole). The autoclave was sealed up and purged three times with nitrogen (200 psi). The reaction mixture was heated with stirring (200 rpm) at a ramp rate of 3° C./min to 150° C. Dehydration was carried out from 150° C. to 208° C. by allowing water to distill out through the condensor. Approximately 39 ml of a distillate (97% water) was collected over the course of 45 minutes. At this point in the reaction, dichlorobenzene (DCB; 148.48 g; 1.01 moles) in NMP (40.0 g; 0.40 moles) was charged to the reaction followed by an NMP (60.0 g; 0.60 moles) wash of the charging vessel.

The reaction mixture was then heated to 250° C. and held at 250° C. for 120 minutes. The was followed by the addition of 5.89 g (0.01 mole) of 2-(3',5'-di-tert-butyl-2'-hydroxyphenyl)-5-(4''-bromophenylsulfonyl)-benzotriazole (synthesized as described in Example X) in 70 g (0,706 mole) of NMP to the autoclave. The reaction mixture was held for an additional 30 minutes at 250° C. (220 psig) and then cooled to 25° C.

The polymer product was collected on filter paper and washed twice with 2 liters of acetone to remove any unreacted stabilizer. The acetone-washed product was again washed twice with 2 liters of hot (about 100° C.) deionized water followed by drying in a vacuum oven (25 torr) at 120° C. for 16 hours. A total of 103.0 g polymer was recovered. The polymer had an extrusion rate (measured at 315° C. by the method of ASTM D 1238-86, condition 315/0.345, modified to use an office having a length of 1.25 inches and a 5 minute preheat *time) of 11.6 g/10 min. A film sample made from the product showed the presence of the hydroxyphenylbenzotriazole moiety when analyzed by UV spectroscopy.

EXAMPLE XII

This example illustrates that a poly(phenylene sulfide) that is chemically bonded to a sulfur-containing derivative of hydroxyphenylbenzotriazole can also be made by adding the halo-substituted sulfur-containing derivative of hydroxyphenylbenzotriazole reagent at a different stage of the polymerization process.

The condition of *the run was identical to that described in Example XI except that 2-(3',5'-di-tert-butyl-2'-hydroxyphenyl)-5-(4''-bromophenylsulfonyl)benzotriazole was added to the autoclave before the reaction temperature reached 250° C. and the reaction mixture was held at 250° C. for 2 hours. The product was worked up as described in Example XI. The recovered product weighed 103.0 g.

The extrusion rate of this product was 108.9 g/10 minutes. A control reaction run under these same conditions but without adding the 2-(3',5'-di-tert-butyl-2'-hydroxyphenyl)-5-(4''-bromophenylsulfonyl)benzo-triazole produced a product with an extrusion rate of 9.2 g/10 minutes.

Furthermore, a film sample made from a blend of the invention product with PPS A showed the presence of the hydroxyphenylbenzotriazole moiety when analyzed by UV spectroscopy.

EXAMPLE XIII

This example demonstrates that compositions comprising a poly(phenylene sulfide) polymer chemically bonded to a sulfur-containing derivative of hydroxyphenylbenzotriazole (hereinafter referred to as PPS-S derivative) are resistant to UV-induced photodegradation.

Photodegradation tests of the inventive compositions were carried out by the same procedure as described in Example IV using the polymer made in Example XI (run 51, Table IX). Table IX also shows the results of photodegradation of blends of 30% of PPS-S derivative and 70% PPS A (run 52), of 50% PPS-S derivative and 50% PPS A (run 53), and of 75% PPS-S derivative and 25% PPS A (run 54). The stabilizer concentrations in the films made from the three resin blends were estimated by UV spectrophotometry, and the estimates are reported in Table IX. Inhomogeneities in the blends cause deviations of measured concentrations from the expected values.

TABLE IX

Photodegradation of Poly(phenylene sulfide) Chemically Bonded To 2-(3',5'-di-tert-butyl-2'-hydroxyphenyl)-5-(phenyl-sulfonyl)benzotriazole

| Run | S-derivative In Resin[a] | ΔE |
|---|---|---|
| 50 | 0 | 20.0 |
| 51 | 0.0020 | 8.9 |
| 52 | 0.0004 | 11.0 |
| 53 | 0.0007 | 12.0 |
| 54 | 0.0017 | 8.4 |
| 55[b] | 0.0030 | 12.9 |
| 56[b] | 0.0060 | 9.2 |

[a]The amount of UV stabilizer is expressed as moles of stabilizer per repeat unit of PPS polymer in the composition or in the blends (see text for detail).
[b]In runs 55–56, the PPS polymers were made in the presence of 2-(3',5'-di-tert-2'-hydroxyphenyl)-5-chlorobenzotriazole (a commercially available product from Ciba-Geigy Corporation sold under the tradename of Tinuvin 327) instead of the inventive 2-(3',5'-di-tert-butyl-2'-hydroxyphenyl)-5-(4''-bromophenylsulfonyl)benzotriazole.

The results in Table IX indicate that chemically bonding as low as 0.0004 mole (run 52) of the sulfur-containing derivative of hydroxyphenylbenzotriazole per repeat unit of PPS resin resulted in a significant reduction in ΔE. The ΔE further decreased to less than 9.0 as the stabilizer content was increased to 0.0017 mole (run 54). Incorporation of a commercially available non-sulfur-containing derivative of hydroxyphenylbenzotriazole into PPS resins also decreased the ΔE (runs 55–56). However, for comparable reductions, considerably higher incorporation of the commercially available non-sulfur-containing derivative of hydroxyphenylbenzotriazole was required (runs 51–54 compared with runs 55–56).

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A process for synthesizing a sulfur-containing derivative of hydroxyphenylbenzotriazole comprising the steps of:
   (1) contacting a sulfur-containing aromatic compound with a hydroxyphenylbenzotriazole derivative having the formula of:

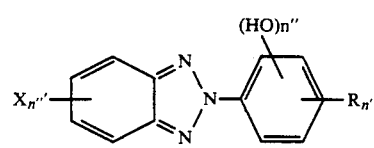

in the presence of a polar organic compound to form an aryl sulfide derivative of hydroxyphenylbenzotriazole having the formula of:

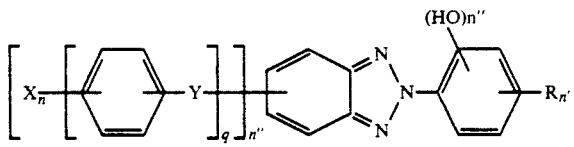

wherein said sulfur-containing aromatic compound is selected from the group consisting of $X_n$—Ar—SH, $X_n$—AR—SM, and combinations thereof; Ar is a phenyl group; M is an alkali metal; X is a substituent selected from the group consisting of hydrogen, chlorine, bromine, iodine, fluorine, cyano, alkyl, phenyl group, biphenyl group, arythio, amine, ketone, aldehyde, alkoxy, hydroxy, carboxylic acid group, oligomer, and combinations thereof; X' is selected from the group consisting of chlorine, bromine, iodine, fluorine, and combinations thereof; n is a whole number from 1 to 5; n' is a whole number from 0 to 4; n" is a whole number from 1 to 2 and each n" can be the same or different; q is an integer of 1 to 10; each Y is selected from the group consisting of —S(O)(O)—, —S(O)—, —S—, and combinations thereof; each R can be the same or different and each is selected from the group consisting of hydrogen, alkyl group, alkenyl group, aralkyl group, alkaryl group and combinations thereof; said polar organic compound substantially dissolves the reactants under reaction conditions; organic molecule having 2 to about 10 repeat units of a monomer unit; and each X, X', Y, and R can be at any available position of said phenyl group; and (2) contacting said aryl sulfide derivative of hydroxyphenylbenzotriazole with an oxidizing agent which oxidizes said aryl sulfide of hydroxyphenylbenzotriazole to a second sulfur-containing derivative of hydroxyphenylbenzotriazole selected from the group consisting of an aryl sulfoxide derivative of hydroxyphenylbenzotriazole, an aryl sulfone derivative of hydroxyphenylbenzotriazole, and mixtures thereof.

2. A process according to claim 1 wherein X is selected from the group consisting of hydrogen, chlorine, bromine, iodine, fluorine, and combinations thereof.

3. A process according to claim 1 wherein said sulfur-containing derivative of hydroxyphenylbenzotriazole is selected from the group consisting of 2-(3',5'-di-tert-butyl-2'-hydroxyphenyl)-5-(phenylthio)benzotriazole, 2-(2'-hydroxyphenyl)-5-(phenylthio)benzotriazole, 2-(3',5'-di-tert-butyl-2'-hydroxyphenyl)-5-(4"-aminophenylthio)benzotriazole, 2-(3',5'-di-tert-cumyl-2'-hydroxyphenyl)-5-(phenylthio)benzotriazole, 2-(3',5'-di-tert-butyl-2'-hydroxyphenyl)-5-(4"-bromophenylthio)benzotriazole, and mixtures thereof.

4. A process according to claim 1 wherein said sulfur-containing derivative of hydroxyphenylbenzotriazole is selected from the group consisting of 2-(3',5'-di-tert-butyl-2'-hydroxyphenyl)-5-(phenylsulfinyl)benzotriazole, 2-(3',5'-di-tert-butyl-2'-hydroxyphenyl)-5-(phenylsulfonyl)benzotriazole, 2-(2'-hydroxyphenyl)-5-(phenylsulfinyl)benzotriazole, 2-(2'-hydroxyphenyl)-5-(phenylsulfonyl)benzotriazole, 2-(3,',5'-di-tert-butyl-2'-hydroxyphenyl)-5-(4"-aminophenylsulfinyl)benzotriazole, 2-(3',5'-di-tert-butyl-2'-hydroxyphenyl)-5-(4"-aminophenylsulfonyl)benzotriazole, 2-(3',5'-di-tert-cumyl-2'-hydroxyphenyl)-5-(phenylsulfinyl)benzotriazole, 2-(3',5'-di-tert-cumyl-2'-hydroxyphenyl)-5-(phenylsulfonyl)benzotriazole, 2-(3',5'-di-tert-butyl-2'-hydroxylphenyl)-5-(4"-bromophenylsulfinyl)benzotriazole, 2-(3',5'-di-tert-butyl-2'-hydroxylphenyl)-5-(4"-bromophenylsulfonyl)benzotriazole, and mixtures thereof.

5. A process according to claim 1 wherein said process further comprises recovering said aryl sulfide derivative of hydroxyphenylbenzotriazole.

6. A process according to claim 1 wherein said process further comprises recovering said aryl sulfone derivative o hydroxyphenylbenzotriazole.

7. A process according to claim 1 wherein said process further comprises recovering said mixture of aryl sulfoxide derivative of hydroxyphenylbenzotriazole and aryl sulfone derivative of hydroxyphenylbenzotriazole.

8. A process according to claim 1 wherein said aryl sulfide derivative of benzotriazole is 2-(3',5'-di-tert-butyl-2'-hydroxyphenyl)-5-(phenylthio)benzotriazole.

9. A process according to claim 1 wherein said aryl sulfone derivative of benzotriazole is 2-(3',5'-di-tert-butyl-2'-hydroxyphenyl)-5-(phenylsulfonyl)benzotriazole.

10. A process according to claim 1 wherein said aryl sulfoxide is 2-(3',5'-di-tert-butyl-2'-hydroxyphenyl)-5-(phenylsulfinyl)benzotriazole.

11. A process according to claim 1 wherein said aryl sulfone derivative of benzotriazole is 2-(3',5'-di-tert-butyl-2'-hydroxyphenyl)-5-(4"-bromophenylsulfonyl)-benzotriazole.

12. A process according to claim 1 wherein said hydroxyphenylbenzotriazole derivative is 2-(3',5'-di-tert-butyl-2'-hydroxyphenyl)-5-chlorobenzotriazole.

13. A process according to claim 1 wherein said thiophenolic compound is thiophenol.

14. A process according to claim 1 wherein said polar organic compound is selected from the group consisting of amides, lactams, sulfones and mixtures thereof.

15. A process according to claim 14 wherein said polar organic compound is N-methyl-2-pyrrolidone.

16. A process according to claim 1 wherein said step (1) process is carried out in the presence of a basic compound.

17. A process according to claim 16 wherein said basic compound is sodium hydroxide.

18. A process according to claim 1 wherein said step (1) process is carried out in the presence of water.

19. A process according to claim 1 wherein the molar ratio of said sulfur-containing aromatic compound to said hydroxyphenylbenzotriazole derivative is in the range of from 0.5:1 to about 4:1.

20. A process according to claim 19 wherein said molar ratio is from about 1:1 to about 2:1.

21. A process according to claim 1 wherein the molar ratio of said polar organic compound of step (1) to said hydroxyphenylbenzotriazole derivative is in the range of from about 0.1:1 to about 100:1.

22. A process according to claim 21 wherein said molar ratio is in the range of from a 05:1 to 20:1.

23. A process according to claim 16 wherein the molar ratio of said basic compound to said hydroxyphenylbenzotriazole derivative is in the range of from about 0.5:1 to about 4:1.

24. A process according to claim 23 wherein said molar ratio is from about 1:1 to about 2:1.

25. A process according to claim 18 wherein the molar ratio of said water to said hydroxyphenylbenzotriazole is in the range of from about 0.0001:1 to about 20:1.

26. A process according to claim 1 wherein said oxidizing agent is m-chloroperbenzoic acid.

27. A process according to claim 1 wherein said oxidizing agent is hydrogen peroxide.

28. A process according to claim 1 wherein said step (2) process is carried out in the presence of a catalyst wherein said catalyst promotes oxidation of said aryl sulfide derivative.

29. A process according to claim 28 wherein said catalyst is tungstic acid.

30. A process according to claim 1 wherein said step (2) process is carried out in the presence of a solvent.

31. A process according to claim 30 wherein said solvent is methylene chloride.

32. A process according to claim 1 wherein the molar ratio of said oxidizing agent to said aryl sulfide derivative of hydroxyphenylbenzotriazole is in the range of from about 1:1 to about 20:1.

33. A process according to claim 32 wherein said molar ratio is from 1:1 to 10:1.

34. A process according to claim 30 wherein the molar ratio of said solvent to said aryl sulfide derivative of hydroxyphenylbenzotriazole is in the range of from about 10:1 to about 1000:1.

35. A process according to claim 34 wherein said molar ratio is in the range of from 20:1 to 200:1.

36. A process according to claim 1 wherein said process in step (1) is carried out at a temperature in the range of from about 5° C. to about 500° C.

37. A process according to claim 36 wherein said temperature is in the range of from 150° C. to 300° C.

38. A process according to claim 1 wherein said process in step (1) is carried out at a temperature in the range of from about 5° C. to about 500° C.

39. A process according to claim 38 wherein said temperature is in the range of from 15° C. to 90° C.

40. A process according to claim 1 wherein said process in step (1) is carried out under a pressure in the range of from about 1 atmosphere to about 500 atmospheres.

41. A process according to claim 40 wherein said pressure is in the range of from 1 atmosphere to 15 atmospheres.

42. A process according to claim 1 wherein said process in step (1) is carried out under a pressure in the range of from about 1 atmosphere to about 500 atmospheres.

43. A process according to claim 42 wherein said pressure is in the range of from 1 atmosphere to 15 atmospheres.

44. A process according to claim 1 wherein said process in step (1) is carried out for a period of at least about 1 minute.

45. A process according to claim 44 wherein said period is in the range of from 10 minutes to 15 hours.

46. A process according to claim 1 wherein said process in step (2) is carried out for a period of at least about 1 minute.

47. A process according to claim 46 wherein said period is in the range of from 10 minutes to 15 hours.

48. A process for synthesizing 2-(3',5'-di-tert-butyl-2'-hydroxyphenyl)-5-(phenylsulfonyl)benzotriazole comprising the steps of: (1) contacting thiophenol with 2-(3',5'-di-tert-butyl-2'-hydroxyphenyl)-5-chlorobenzotriazole in the presence of a basic compound and N-methyl-2-pyrrolidone at 150° C. to 300° C. under 1 atmosphere to 15 atmospheres for 10 minutes to 15 hours wherein the molar ratio of said thiophenol to said 2-(3',5'-di-tert-butyl-2'-hydroxyphenyl)-5-chlorobenzotriazole is about 1:1, the molar ratio of sodium hydroxide to 2-(3',5'-di-tert-butyl-2'-hydroxyphenyl)-5-chlorobenzotriazole is about 1:1; the molar ratio of said N-methyl-2-pyrrolidone to said 2-(3',5'-di-tert-butyl-2'-hydroxyphenyl)-5-chlorobenzotriazole is from 0.5:1 to 20:1; and (2) contacting said 2-(3',5'-di-tert-butyl-2'-hydroxyphenyl)-5-(phenylthio)benzotriazole with m-chloroperbenzoic acid in methylene chloride at 15° C. to 90° C. under 1 atmosphere to 15 atmospheres for 10 minutes to 15 hours wherein the molar ratio of said m-chloroperbenzoic acid to said 2-(3',5'-di-tert-butyl-2'-hydroxyphenyl)-5-(phenylthio)benzotriazole is from 1:1 to 10:1 and the molar ratio of said methylene chloride to said 2-(3',5'-di-tert-butyl-2'-hydroxyphenyl)-5-(phenylthio)benzotriazole is from 20:1 to 200:1; wherein said basic compound is selected from the group consisting of tetramethylammonium hydroxide, potassium hydroxide, sodium hydroxide, lithium hydroxide, magnesium hydroxide, calcium hydroxide, ammonium hydroxide, lithium carbonate, sodium carbonate, potassium carbonate, calcium carbonate, magnesium carbonate, and mixtures thereof.

49. A process according to claim 48 wherein said 2-(3',5'-di-tert-butyl-2'-hydroxyphenyl)-5-(phenylthio)benzotriazole is further converted to a mixture comprising 2-(3',5'-di-tert-butyl-2'-hydroxyphenyl)-5-(phenylsulfinyl)benzotriazole and 2-(3',5'-di-tert-butyl-2'-hydroxyphenyl)-5-(phenylsulfonyl)benzotriazole by reacting said 2-(3',5'-di-tert-butyl-2'-hydroxyphenyl)-5-(phenylthio)benzotriazole with hydrogen peroxide in 2-propanol in the presence of a catalytic amount of tungstic acid at 15° C. to 90° C. under 1 atmosphere to 15 atmospheres for 10 minutes to 15 hours wherein the molar ratio of said hydrogen peroxide to said 2-(3',5'-di-tert-butyl-2'-hydroxyphenyl)-5-(phenylthio)benzotriazole is from 20:1 to 200:1.

50. A process according to claim 48 wherein said 2-(3'-5'-di-tert-butyl-2'-hydroxyphenyl)-5-(phenylthio)benzotriazole is further converted to 2-(3',5'-di-tert-butyl-2'-hydroxyphenyl)-5-(4''-bromophenylsulfonyl)benzotriazole by the steps of: (1) contacting said 2-(3',5'-di-tert-butyl-2'-hydroxyphenyl)-5-(phenylthio)benzotriazole with bromine in carbon tetrachloride at a temperature in the range of from about 0° C. to about 50° C. wherein the molar ratio of bromine to 2-(3'-5'-di-tert-butyl-2'-hydroxyphenyl)-5-(phenylthio)benzotriazole is in the range of from about 1:1 to about 20:1 to prepare 2-(3',5'-di-tert-butyl-2'-hydroxyphenyl)-5-(4''-bromophenylthio)benzotriazole; (2) removing said bromine and carbon tetrachloride from said 2-(3',5'-di-tert-butyl-2'-hydroxyphenyl)-5-(4''-bromophenylthio)benzotriazole; (3) contacting said 2-(3',5'-di-tert-butyl-2'-hydroxyphenyl)-5-(4''-bromophenylthio)benzotriazole with m-chloroperbenzoic acid in methylene chloride at 15° C. to 90° C. under 1 atmosphere to 15 atmospheres for 10 minutes to 15 hours wherein the molar ratio of said m-chloroperbenzoic acid to said 2-(3',5'-di-tert-butyl-2'-hydroxyphenyl)-5-(4''-bromophenylthio)benzotriazole is from 1:1 to 10:1 and the molar ratio of said methylene chloride to said 2-(3',5'-di-tert-butyl-2'-hydroxyphenyl)-5-(4''-bromophenylthio)benzotriazole is from 2:1 to 200:1.

* * * * *

UNITED STATES PATENT AND TRADEMARK OFFICE
CERTIFICATE OF CORRECTION

PATENT NO. : 5,319,091
DATED : June 7, 1994
INVENTOR(S) : Paul J. DesLauriers et al It is certified that error appears in the above-identified patent and that said Letters Patent is hereby corrected as shown below:

Column 25, line 18, delete "arythio" and insert therefor ---arylthio---.

Signed and Sealed this

Twenty-seventh Day of September, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,319,091

DATED : June 7, 1994

INVENTOR(S) : Paul J. DesLauriers, et. al.

It is certified that error appears in the above-identified patent and that said Letters Patent is hereby corrected as shown below:

Column 25, lines 33-34, delete "organic molecule having 2 to about 10 repeat units of a monomer unit;".

Column 28, lines 7-8, delete "sodium hydroxide" and insert therefor -- basic compound--.

Signed and Sealed this

Eighth Day of November, 1994

Attest:

BRUCE LEHMAN

Attesting Officer

Commissioner of Patents and Trademarks